US011096932B2

(12) United States Patent
Raju et al.

(10) Patent No.: US 11,096,932 B2
(45) Date of Patent: Aug. 24, 2021

(54) METHODS AND COMPOSITIONS FOR INCREASING MUCUS CLEARANCE

(71) Applicant: THE UAB RESEARCH FOUNDATION, Birmingham, AL (US)

(72) Inventors: Sammeta Vamsee Raju, Homewood, AL (US); Lawrence Rasmussen, Homewood, AL (US); Steven Mark Rowe, Birmingham, AL (US)

(73) Assignee: THE UAB RESEARCH FOUNDATION, Birmingham, AL (US)

( * ) Notice: Subject to any disclaimer, the term of this patent is extended or adjusted under 35 U.S.C. 154(b) by 0 days.

(21) Appl. No.: 16/338,150

(22) PCT Filed: Sep. 29, 2017

(86) PCT No.: PCT/US2017/054405
§ 371 (c)(1),
(2) Date: Mar. 29, 2019

(87) PCT Pub. No.: WO2018/064529
PCT Pub. Date: Apr. 5, 2018

(65) Prior Publication Data
US 2019/0275020 A1 Sep. 12, 2019

Related U.S. Application Data

(60) Provisional application No. 62/401,667, filed on Sep. 29, 2016.

(51) Int. Cl.
*A61K 31/444* (2006.01)
*A61P 11/12* (2006.01)
*A61K 9/00* (2006.01)
*A61K 9/127* (2006.01)
*A61K 45/06* (2006.01)
*A61K 31/4402* (2006.01)

(52) U.S. Cl.
CPC .......... *A61K 31/444* (2013.01); *A61K 9/0073* (2013.01); *A61K 9/127* (2013.01); *A61K 31/4402* (2013.01); *A61K 45/06* (2013.01); *A61P 11/12* (2018.01)

(58) Field of Classification Search
CPC .............. A61K 31/444; A61K 31/4402; A61K 9/0073; A61K 9/127; A61K 45/06; A61P 11/12
See application file for complete search history.

(56) References Cited

U.S. PATENT DOCUMENTS

| | | | |
|---|---|---|---|
| 5,516,785 A | 5/1996 | Zoltewicz et al. | |
| 5,602,257 A | 2/1997 | Zoltewicz et al. | |
| 5,734,059 A | 3/1998 | Watanabe et al. | |
| 5,741,802 A | 4/1998 | Kem et al. | |
| 5,840,906 A | 11/1998 | Zoltewicz et al. | |
| 5,977,144 A | 11/1999 | Meyer et al. | |
| 6,077,680 A | 6/2000 | Kem et al. | |
| 6,630,491 B1 | 10/2003 | Zoltewicz et al. | |
| 8,093,269 B2 | 1/2012 | Kem et al. | |
| 8,592,458 B2 | 11/2013 | Kem et al. | |
| 9,150,558 B2 | 10/2015 | Kem et al. | |
| 9,682,969 B2 * | 6/2017 | Cole | A61P 21/04 |
| 2005/0159454 A1 | 7/2005 | Kem et al. | |
| 2005/0288333 A1 | 12/2005 | Kem | |
| 2009/0215705 A1 | 8/2009 | Kem et al. | |
| 2012/0094943 A1 | 4/2012 | Kem et al. | |
| 2014/0343042 A1 | 11/2014 | Kem et al. | |
| 2019/0111038 A1 * | 4/2019 | Solis Herrera | A61K 31/4439 |

FOREIGN PATENT DOCUMENTS

| | | | |
|---|---|---|---|
| WO | 2004052365 A2 | 6/2004 | |
| WO | WO-2004052365 A2 * | 6/2004 | ............. A61P 27/02 |
| WO | 2008036293 A1 | 3/2008 | |

OTHER PUBLICATIONS

Kamel et al. (Contribution of α7 nicotinic receptor to airway epithelium dysfunction under nicotine exposure), (Year: 2013).*
Srinivasan et al. ( Mucociliary dysfunction in HIV and smoked substance abuse) (Year: 2015).*
PCT/US2017/054405, International Preliminary Report on Patentability, dated Apr. 11, 2019, 7 pages.
PCT/US2017/054405, International Search Report and Written Opinion, dated Dec. 28, 2017, 9 pages.
Albuquerque et al., "Mammalian Nicotinic Acetylcholine Receptors: From Structure to Function," Physiol. Rev. 89(1):73-120 (2009).
"Bradanicline", accessed on https://en.wikipedia.org/wiki/Bradanicline, available on Sep. 26, 2017, last edited on Oct. 4, 2020.
Bustamante-Marin,et al., "Cilia and Mucociliary Clearance", Cold Spring Harb Perspect Bio, (2017) vol. 9:a028241.
Chinnapaiyan et al., "Mucociliary dysfunction in HIV and smoked substance abuse", frontiers in Microbiology, vol. 6, Article 1052, Oct. 2015.
Conger Jr. et al., "Comparison of Cystic Fibrosis Transmembrane Conductance Regulator (CFTR) and Ciliary Beat Frequency Activation by the CFTR Modulators Genistein, VRT-532, and $UC_{CF}$-152 in Primary Sinonasal Epithelial Cultures", JAMA Otolaryngol. Head Neck Surg. 139(8): 822-827 (2013).
Fahy, et al., "Airway Mucus Function and Dysfunction", N Engl J Med., 363(23): 2233-2247 (2010).
Lambert, et al., "Cystic fibrosis transmembrane conductance regulator activation by roflumilast contributes to therapeutic benefit in chronic bronchitis", Am J Respir Cell Mol Biol 2014, 50:549-558.
Maouche, et al., "Contribution of α7 nicotinic receptor to airway epithelium dysfunction under nicotine exposure", PNAS, vol. 110, No. 10, Mar. 5, 2013, pp. 4099-4104.

(Continued)

Primary Examiner — Snigdha Maewall
(74) Attorney, Agent, or Firm — Kilpatrick Townsend & Stockton LLP

(57) ABSTRACT

Provided herein are methods of increasing mucus clearance in a subject having decreased mucus clearance. Also provided are methods of treating or preventing a respiratory disorder.

15 Claims, 12 Drawing Sheets

(56) References Cited

OTHER PUBLICATIONS

Raju et al., "A ferret model of COPD-related chronic bronchitis," JCI Insight 1:e87536 (2016).
Raju et al. "Cigarette smoke induces systemic defects in cystic fibrosis transmembrane conductance regulator function," Am J Respir Crit Care Med, 188:1321-1330 (2013).
Raju et al. "The Cystic Fibrosis Transmembrane Conductance Regulator Potentiator Ivacaftor Augments Mucociliary Clearance Abrogating Cystic Fibrosis Transmembrane Conductance Regulator Inhibition by Cigarette Smoke," Am J Respir Cell Mol Biol, 56:99-108 (2017).
Raju et al. "Acquired Cystic Fibrosis Transmembrane Conductance Regulator Dysfunction in Chronic Bronchitis and Other Diseases of Mucus Clearance," Clin. Chest Med. 37: 147-158 (2016).
Raju et al., "Acquired CFTR Dysfunction in a Novel Ferret Model of COPD", In Pediatric Pulmonology, Wiley-Blackwell, 246-246 online abstract (2014).
Rasmussen, et al., "Pharmacologic Targeting of Alpha7 Nicotinic Receptors to Treat COPD-Related Chronic Bronchitis", Am J Respir Crit Care Med, 195:A2426 (2017).
Rowe et al., "DeltaF508 CFTR processing correction and activity in polarized airway and non-airway cell monolayers", Pulm Pharmacol Ther 23:268-278 (2010).
Solomon et al. "An international randomized multicenter comparison of nasal potential difference techniques", Chest, 138:919-928 (2010).
Van Goor et al. "Rescue of CF airway epithelial cell function in vitro by a CFTR potentiator VX-770", Proc Natl Acad Sci U S A, 106:18825-18830 (2009).

\* cited by examiner

METHODS AND COMPOSITIONS FOR INCREASING MUCUS CLEARANCE

This application claims the benefit of U.S. Provisional Application No. 62/401,667, filed Sep. 29, 2016, hereby incorporated in its entirety by this reference.

BACKGROUND

Mucus clearance (MCC) is a critical defense mechanism of the airways to maintain surface hygiene. Deterioration of MCC is a key contributor to the pathogenesis of respiratory diseases.

SUMMARY

Provided herein are methods of increasing mucus clearance in a subject having decreased mucus clearance. Also provided are methods of treating or preventing a respiratory disorder. The methods comprise administering to the subject an effective amount of α-7 nicotinic acetylcholine receptor (nAChR) agonist.

DESCRIPTION

Figure 1A:
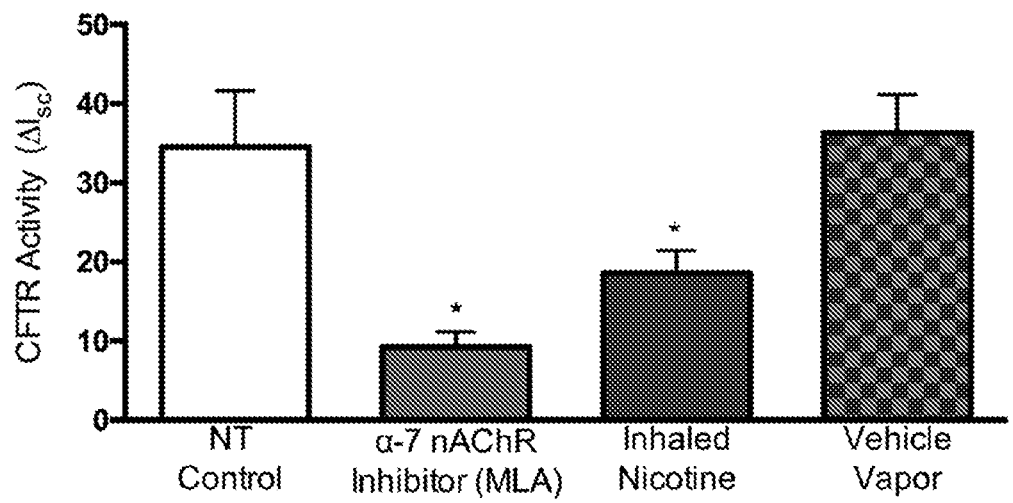
FIG. 1A shows the effects of treating primary human bronchial epithelial (HBE) cells with vehicle (water vapor), α-7 nAChR inhibitor MLA, and nicotine vapor with and without α-7 nAChR. Forskolin-induced anion transport via CFTR channels that is needed for optimum MCC is shown. These data suggest that loss of α-7 nAChR signaling impacts CFTR function and as such α-7 nAChR activation restores CFTR function

Provided herein are methods for increasing mucus clearance (MCC) in a subject having decreased MCC comprising administering an α-7 nicotinic acetylcholine receptor (nAChR) agonist to the subject.

Also provided herein are methods for treating or preventing a respiratory disorder in a subject comprising administering an α-7 nAChR agonist to the subject.

As used throughout, a nAChR(s) is a cholinergic receptors found in the central nervous system, peripheral nervous system, skeletal muscle and airways, to name a few. As used throughout, an agonist is an agent, for example, a chemical or a compound, that binds to a α-7 nAChR and activates the receptor to produce a biological response, for example, induction of ion channel activity. See, for example, Albuquerque et al. "Mammalian Nicotinic Acetylcholine Receptors: From Structure to Function," Physiol. Rev. 89(1): 73-120 (2009), hereby incorporated in its entirety by this reference. Optionally, the agonist selectively binds to α-7 nAChR. In some examples, the α-7 nAChR agonist is an agent that that mimics the action of nicotine and/or acetylcholine (Ach) at nAchRs. Any α-7 nAChR agonist, including a partial agonist, a full agonist or an allosteric modulator of α-7 nAChR, can be used in the methods provided herein. In some methods, one or more α-7 nAChR agonists can be used.

For example, the α-7 nAChR agonist can be an anabaseine (3,4,5,6-Tetrahydro-2,3'-bipyridine) derivative. For example, and not to be limiting, the anabaseine derivative can be a compound having Formula I

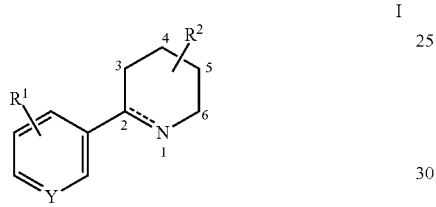

I or a pharmaceutically acceptable salt thereof, wherein the dotted line between the 1- and 2-positions of the 6-membered cyclic ring containing nitrogen atom represents an optional bond; Y is nitrogen or carbon; $R^1$ is hydrogen or $C_1$-$C_4$ alkyl; and $R^2$ is hydrogen, $C_1$-$C_4$ alkyl, or =CH—X, wherein X is napthyl optionally substituted by N,N-dialkylamino having 1 to 4 carbons in each of the alkyls, styryl optionally substituted by N,N-dialkylamino having 1 to 4 carbons in each of the aklyls, furyl, furylacrolyl or

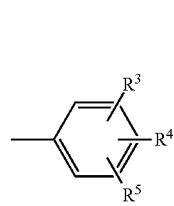

wherein $R^3$, $R^4$, and $R^5$ are each selected from hydrogen, $C_1$-$C_4$ alkyl, $C_1$-$C_6$ alkoxy optionally substituted by N,N dialkylamino having 1 to 4 carbons in each of the alkyls, amino, cyano, N,N-dialkylamino having 1 to 4 carbons in each of the alkyls, halo, hydroxyl and nitro.

As used throughout, halo means flouro, chloro, bromo and iodo. $C_3$-$C_4$ alkyl and $C_3$-$C_6$ alkoxy groups can be straight or branched. In some examples, there is a double bond between the 1- and 2-positions of the 6-membered cyclic ring containing nitrogen atom. In some examples, Y is nitrogen. In other examples, when $R^1$ or $R^2$ is $C_1$-$C_4$ alkyl, it is methyl. In some examples, when $R^3$, $R^4$ or $R^5$ is $C_1$-$C_6$ alkoxy, it is methoxy.

In some examples, the compound of Formula I is a compound having Formula II.

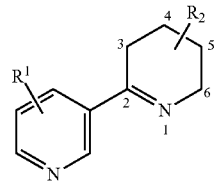

II or a pharmaceutically acceptable salt thereof; wherein $R^1$ is hydrogen or $C_1$-$C_4$ alkyl; $R^2$ is =CH—X, wherein X is napthyl optionally substituted by N,N-dialkylamino having 1 to 4 carbons in each of the alkyls, styryl optionally substituted by N,N-dialkylamino having 1 to 4 carbons in each of the aklyls, furyl, furylacrolyl or

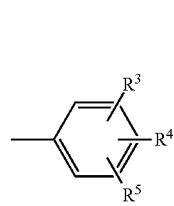

wherein $R^3$, $R^4$, and $R^5$ are each selected from hydrogen, $C_1$-$C_4$ alkyl, $C_1$-$C_6$ alkoxy optionally substituted by N,N dialkylamino having 1 to 4 carbons in each of the alkyls, amino, cyano, N,N-dialkylamino having 1 to 4 carbons in each of the alkyls, halo, hydroxyl and nitro. In some examples, $R^3$, $R^4$ and $R^5$ are not all hydrogen and when two of $R^3$, $R^4$ and $R^5$ are methyl, chloro or methoxy, they are not para to each other. In other examples, when $R^1$ is hydrogen or methyl, $R^2$ is not 1-methyl benzylidene or (4-dimethylamine) benzylidene.

In some examples, the compound is a compound of Formula II, wherein X is

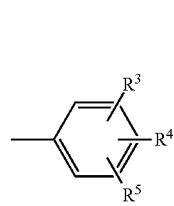

and wherein one or more of $R^3$, $R^4$ and $R^5$ are selected from the group consisting of amino, hydroxyl, chloro, cyano, diethylamino, methyl, methoxy, and nitro. In other examples, $R^3$, $R^4$ and $R^5$ are all methoxy. In some examples, $R^3$ and $R^4$ are both methoxy. In some examples, $R^3$ and $R^5$ are both methoxy.

In some examples, the compound of Formula I is a compound having Formula III (GTS-21) or a pharmaceutically acceptable salt thereof.

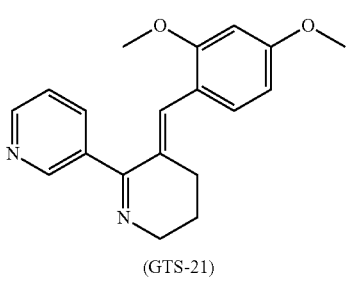

Formula III (GTS-21)

The compound of Formula III is also known as GTS-21, 3-(2,4-dimethoxybenzylidene) anabaseine and DMXBA. Other examples of α-7 nAChR agonists include, but are not limited to, any of the compounds set forth as α-7 nAChR agonists in U.S. Pat. Nos. 5,741,802, 5,977,144, 6,077,680, 5,734,059, 6,630,491, 5,516,785, 8,093,269, 9,150,558, U.S. Patent Application Publication No. 2009/0215705, U.S. Patent Application Publication No. 2005/0288333, U.S. Patent Application Publication No. 2005/0159454, U.S. Patent Application Publication No. 2012/0094943, U.S. Patent Application Publication No. 2014/0343042, all of which are incorporated herein, in their entireties, by this reference.

Additional examples of α-7 nAChR agonists that can be used in the methods provided herein include, but are not limited to, the demethylated active metabolite of GTS-21, (4-0H-GTS-21), A-582941, AR-R1779, TC-1698, Bradanicline, Encenicline, PHA-543613, PNU-282987, PNU-120596, PHA-709829, SSR-180711, ASM-024, Tropisetron, WAY-317538, anabasine, acetylcholine, nicotine, epiboxidine, choline, ICH-3, TC-6683, AZD-1446, AZD-0328, JNJ-39393406. Pharmaceutically acceptable salts of any of the nAChR agonists provided herein can be used in the methods provided herein. Derivatives and analogs of the α-7 nAChR agonists provided herein can also be used.

As used herein, the term pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds provided herein, for example, pharmaceutically acceptable salts of a compound of Formula I, include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, trifluoroacetic acid, undecanoate, valerate salts, and the like.

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography. Compounds of Formula I and methods of making the compounds of Formula I are also described in U.S. Pat. No. 5,741,802, which is incorporated herein in its entirety.

In the methods provided herein, a decrease or a defect in MCC can be associated with one or more respiratory disorders. A decrease or a defect in MCC can contribute to the progression of chronic lung or pulmonary diseases including cystic fibrosis, asthma, chronic obstructive pulmonary disease (COPD), bronchitis, a respiratory allergy and a respiratory infection, to name a few. Therefore the methods provided herein can be used to increase MCC in a subject having one or more respiratory disorders selected from the group consisting of cystic fibrosis, COPD, asthma, bronchitis, respiratory allergy and a respiratory infection. In any of the methods provided herein, the subject can be a subject diagnosed with one or more respiratory disorders selected from the group consisting of cystic fibrosis, COPD, asthma, bronchitis, respiratory allergy and a respiratory infection.

As used throughout, mucus clearance or mucociliary clearance (MCC) describes the self-cleaning mechanism of the bronchi. The passage of airway in the respiratory tract that conducts air into the lungs main bronchi down to the alveoli, the final branchings of the respiratory tree (which act as the primary gas exchange units of the lung). The alveoli are lined with a moist lining of the airway respiratory epithelium bearing cilia (hair-like structures) on its surface (cilia). The cilia are surrounded by mucus, or epithelial lining fluid (ELF), the composition of which is tightly regulated. The mucus helps maintain epithelial moisture, traps particulate material and pathogens moving through the airway, and determines how well mucociliary clearance works. As used throughout, an increase in MCC can be about a 10%, 20%, 30%, 40%, 50%, 60%, 70%, 80%, 90%, 100%, 200%, 300%, 400% increase or greater.

In the methods provided herein, one of skill in the art would know how to select a subject with a defect or a decrease in MCC as compared to a control. The control can be a subject or a sample from a subject without a defect or a decrease in MCC. The control can also be a subject or a sample from a subject that has been successfully treated for a decrease in MCC. The control can also be a known reference sample or value. As used throughout, a subject with a decrease in MCC can be a subject with about a 10%, 20%, 30%, 40%, 50%, 60%, 70%, 80%, or a 90% decrease or greater, as compared to control.

For example, the subject could be a subject that has been diagnosed with decreased MCC or a respiratory disorder associated with decreased MCC. The subject can also be a subject that could have a genetic propensity to a respiratory disorder associated with decreased MCC, or could have been exposed to environmental stimuli that cause decreased MCC or a respiratory disorder associated with decreased MCC. For example, the subject could have inhaled a caustic agent such as smoke or chemicals. One or more symptoms of decreased MCC or a respiratory disorder associated with decreased MCC can also be detected. For example, symptoms include, but are not limited to shortness of breath, coughing up thick mucus, wheezing, cough, and diminished exercise tolerance.

Genetic and acquired defects in a calcium-activated chloride channel(s), for example, cystic fibrosis transmembrane conductance regulator (CFTR) channels lead to decreased ion transport by epithelial cells that line airways and other glandular tissues. Reduced ion transport diminishes water transport to the airway lumen causing dehydration of mucosal surface and reduced MCC. Therefore, optionally, a subject with decreased MCC can have impaired or decreased ion transport, for example, CFTR ion transport, as compared to a control.

One of skill in the art would know how to select a subject with a decrease in ion transport as compared to a control. The control can be a subject or a sample from a subject without a defect or a decrease in ion transport. The control can also be a subject or a sample from a subject that has been successfully treated for a decrease in ion transport. The control can also be a known reference sample or value. As used throughout, a subject with a decrease in ion transport can be a subject with about a 10%, 20%, 30%, 40%, 50%, 60%, 70%, 80%, or a 90% decrease or greater, as compared to control. As used throughout, an increase in ion transport can be about a 10%, 20%, 30%, 40%, 50%, 60%, 70%, 80%, 90%, 100%, 200%, 300%, 400% increase or greater, as compared to control.

In some examples, administering an α-7 nAChR agonist increases ion transport through a calcium-activated chloride channel(s), for example, CFTR ion transport, in a subject with decreased MCC. Optionally, the calcium-activated chloride channel is present in the airway of the subject. Optionally, the calcium-activated chloride channel responds to ATP activation. Optionally, the calcium-activated chloride channel is a cAMP-responsive anion channel.

The CFTR is a cAMP-responsive membrane protein and chloride channel that conducts chloride and thiocyanate ions across epithelial cell membranes. Mutations of the CFTR gene affecting chloride ion channel function lead to dysregulation of epithelial fluid transport in the lung, pancreas and other organs, resulting in cystic fibrosis. Complications include thickened mucus in the lungs with frequent respiratory infections, and pancreatic insufficiency giving rise to malnutrition and diabetes. These conditions lead to chronic disability and reduced life expectancy. Therefore, in the methods provided herein, any of the α-7 nAChR agonists provided herein can be used to treat a respiratory disorder, for example, cystic fibrosis or COPD in a subject, by increasing CFTR ion transport in the subject.

Any of the methods provided herein can further comprise administering a second therapeutic agent to the subject. For example, any of the methods provided herein can further comprise administering a second therapeutic agent to increase MCC and/or treat a respiratory disorder, for example, a respiratory disorder selected from the group consisting of cystic fibrosis, asthma, COPD, bronchitis, a respiratory allergy and a respiratory infection. In some examples, administration of an α-7 nAChR agonist and a second therapeutic agent has a synergistic effect.

Any of the methods provided herein can comprise administering to a subject with cystic fibrosis, an α-7 nAChR agonist and one or more CFTR modulators. These include, but are not limited to CFTR modulators, including, but not limited to, ivacaftor (Kalydeco®) lumacaftor (VX-809)/ivacaftor (Okambi®), VX-661, Ataluren (PTC124), 4PBA, VRT-532, N6022, Cavosonstate (N91115), GLPG1837, PTI130, genistein and curcumin. In some examples, the CFTR modulator, for example, a CTFR corrector, is administered at a dosage used to treat cystic fibrosis. For example, 200 mg of lumafactor can be administered every twelve hours to adults and pediatric patients age 12 or older. In another example, 100 mg of lumafactor can be administered every twelve hours to pediatric patients, age 6 through 11 years. In another example, 125 mg of ivacaftor can be administered every twelve hours to adults and pediatric patients age 12 or older. In another example, 125 mg of ivacaftor can be administered every twelve hours to pediatric patients, age 6 through 11 years. In some examples, one or more CTFR modulators are administered. For example, Okambi®, containing 200 mg of lumacaftor and 125 mg of ivacaftor can be administered every twelve hours to adults and pediatric patients age 12 or older. In another example, Okambi®, containing 100 mg of lumacaftor and 125 mg of ivacaftor can be can be administered every twelve hours to pediatric patients, age 6 through 11 years. Optionally, when administered in combination with an α-7 nAChR agonist, the frequency of administration and/or the dosage of one or more CFTR modulators is less than the dosage used to treat cystic fibrosis.

In other examples, any of the methods provided herein can comprise administering to a subject with COPD, an α-7 nAChR agonist and one or more of a bronchodilator (for example, albuterol, levalbuterol, ipratropium, tiotropium, salmeterol, formoterol, arformoterol, indacaterol or aclidinium), a steroid (for example, fluticasone or budesonide), a phosphodiesterase-4 inhibitor (for example, roflumist) or theophylline.

In some examples, any of the methods provided herein can comprise administering to a subject with asthma, an α-7 nAChR agonist and one or more of a bronchodilator, a steroid, Cromolyn, Omalizumab, an inhaled beta2-agonist, a leukotriene modifier or theophylline.

In other examples, an α-7 nAChR agonist can be administered with an anti-infective to treat a subject with a respiratory infection. The respiratory infection can be a bacterial infection, a viral infection, a fungal infection or a parasitic infection. In some examples, the infection is selected from the group consisting of influenza, pneumonia, RSV, rhinovirus, bronchiolitis and sinusitis. Anti-infectives include, but are not limited to antibacterial agents (for example, antibiotics), antiviral agents (for example, oseltamivir, zanamivir or peramivir), antifungal agents and antiparasitic agents.

Throughout, treat, treating, and treatment refer to a method of reducing or delaying one or more effects or symptoms of a respiratory disorder. The subject can be diagnosed with a disease or disorder. Treatment can also refer to a method of reducing the underlying pathology rather than just the symptoms. The effect of the administration to the subject can have the effect of, but is not limited to, reducing one or more symptoms of the respiratory disorder, a reduction in the severity of the respiratory disorder, the complete ablation of the respiratory disorder, or a delay in the onset or worsening of one or more symptoms. For example, a disclosed method is considered to be a treatment if there is about a 10% reduction in one or more symptoms of the disease in a subject when compared to the subject prior to treatment or when compared to a control subject or control value. Thus, the reduction can be about a 10, 20, 30, 40, 50, 60, 70, 80, 90, 100%, or any amount of reduction in between.

As used throughout by prevent, preventing, or prevention is meant a method of precluding, delaying, averting, obviating, forestalling, stopping, or hindering the onset, incidence, severity, or recurrence of the respiratory disease or disorder. For example, the disclosed method is considered to be a prevention if there is a reduction or delay in onset, incidence, severity, or recurrence of a respiratory disease or one or more symptoms of a respiratory disease in a subject susceptible to respiratory disease as compared to control subjects susceptible to respiratory disease that did not receive an α-7 nAChR agonist. The disclosed method is also considered to be a prevention if there is a reduction or delay in onset, incidence, severity, or recurrence of a respiratory disease or one or more symptoms of a respiratory disease in a subject susceptible to a respiratory disease after receiving an an α-7 nAChR agonist as compared to the subject's progression prior to receiving treatment. Thus, the reduction or delay in onset, incidence, severity, or recurrence of a respiratory disease can be about a 10, 20, 30, 40, 50, 60, 70, 80, 90, 100%, or any amount of reduction in between.

As used throughout, by subject is meant an individual. The subject can be an adult subject or a pediatric subject. Pediatric subjects include subjects ranging in age from birth to eighteen years of age. Thus, pediatric subjects of less than about 10 years of age, five years of age, two years of age, one year of age, six months of age, three months of age, one month of age, one week of age or one day of age are also included as subjects. Preferably, the subject is a mammal such as a primate, and, more preferably, a human. Non-human primates are subjects as well. The term subject includes domesticated animals, such as cats, dogs, etc., livestock (for example, cattle, horses, pigs, sheep, goats, etc.) and laboratory animals (for example, ferret, chinchilla, mouse, rabbit, rat, gerbil, guinea pig, etc.). Thus, veterinary uses and medical formulations are contemplated herein.

One or more of the agents described herein can be provided in a pharmaceutical composition. These include, for example, a pharmaceutical composition comprising a therapeutically effective amount of an α-7 nAChR agonist and a pharmaceutical carrier. In some examples, the pharmaceutical composition comprises an α-7 nAChR agonist having the Formula I or a pharmaceutically acceptable salt thereof. In other examples, the pharmaceutical compositions comprises an α-7 nAChR agonist having the Formula II or a pharmaceutically acceptable salt thereof. In other examples, the pharmaceutical compositions comprises an α-7 nAChR agonist having the Formula III or a pharmaceutically acceptable salt thereof.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions described herein can be in a container, for example, and not to be limiting, a nasal sprayer, a nebulizer or an inhaler. Examples of inhalers include, but are not limited to, metered-dose inhalers (manually actuated and breath actuated inhalers), dry powder inhalers and mist inhalers. Examples of nebulizers include, but are not limited to atomizer or compressor nebulizers and ultrasonic nebulizers.

The compositions will include a therapeutically effective amount of the agent described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected agent without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22nd edition, Loyd V. Allen et al, editors, Pharmaceutical Press (2012)

Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the agent(s) described herein suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof are admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, such as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Liposomal compositions comprising any of the compounds provided herein can also be prepared. These compositions can be prepared as a formulation. Optionally, the liposomal composition is formulated for delivery via inhalation. The lipids used in the liposomal compositions can be synthetic, semi-synthetic or naturally-occurring lipids, including phospholipids, tocopherols, steroids, fatty acids, glycoproteins such as albumin, anionic lipids and cationic lipids. The lipids may be anionic, cationic, or neutral. In some examples, the liposomal composition is substantially free of anionic lipids, substantially free of cationic lipids, or both. In some examples, the liposome(s) comprises a lipid selected from the group consisting of phosphatidyl cholines (PCs), phosphatidyl-glycerols (PGs), phosphatidic acids (PAs), phosphatidylinositols (PIs), and phosphatidyl serines (PSs). In another embodiment, the lipid is selected from the group consisting of: egg phosphatidylcholine (EPC), egg phosphatidylglycerol (EPG), egg phosphatidylinositol (EPI), egg phosphatidylserine (EPS), phosphatidylethanolamine (EPE), phosphatidic acid (EPA), soy phosphatidyl choline (SPC), soy phosphatidylglycerol (SPG), soy phosphatidylserine (SPS), soy phosphatidylinositol (SPI), soy phosphatidylethanolamine (SPE), soy phosphatidic acid (SPA), hydrogenated egg phosphatidylcholine (HEPC), hydrogenated egg phosphatidylglycerol (HEPG), hydrogenated egg phosphatidylinositol (HEPI), hydrogenated egg phosphatidylserine (HEPS), hydrogenated phosphatidylethanolamine (HEPE), hydrogenated phosphatidic acid (HEPA), hydrogenated soy phosphatidyl choline (HSPC), hydrogenated soy phosphatidylglycerol (HSPG), hydrogenated soy phosphatidylserine (HSPS), hydrogenated soy phosphatidylinositol (HSPI), hydrogenated soy phosphatidylethanolamine (HSPE), hydrogenated soy phosphatidic acid (HSPA), dipalmitoylphosphatidylcholine (DPPC), dimyristoylphosphatidylcholine (DMPC), dimyristoylphosphatidylglycerol (DMPG), dipalmitoylphosphatidylglycerol (DPPG), distearoylphosphatidylcholine (DSPC), distearoylphosphatidylglycerol (DSPG), dioleylphosphatidylethanolamine (DOPE), palmitoylstearoylphosphatidyl-choline (PSPC), palmitoylstearolphosphatidylglycerol (PSPG), mono-oleoyl-phosphatidylethanolamine (MOPE), tocopherol, ammonium salts of fatty acids, ammonium salts of phospholipids, ammonium salts of glycerides, myristylamine, palmitylamine, laurylamine, stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA), 1,2-bis(oleoyloxy)-3-(trimethylammonio)propane (DOTAP), distearoylphosphatidylglycerol (DSPG), dimyristoylphosphatidylacid (DMPA), dipalmitoylphosphatidylacid (DPPA), distearoylphosphatidylacid (DSPA), dimyristoylphosphatidylinositol (DMPI), dipalmitoylphosphatidylinositol (DPPI), distearoylphospatidylinositol (DSPI), dimyristoylphosphatidylserine (DMPS), dipalmitoylphosphatidylserine (DPPS), distearoylphosphatidylserine (DSPS), and mixtures thereof.

Administration can be carried out using therapeutically effective amounts of the agents described herein for periods of time effective to increase mucosal clearance, increase ion transport and/or treat a respiratory disorder. The effective amount can be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day.

According to the methods taught herein, the subject is administered an effective amount of the agent. The terms effective amount and effective dosage are used interchangeably and refer to any amount necessary or sufficient to produce a desired physiologic response. Effective amounts and schedules for administering the agent can be determined empirically, and making such determinations is within the skill in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the activity of the specific compound employed, the metabolic stability and length of action of that compound, the species, age, body weight, general health, sex and diet of the subject, the mode and time of administration, rate of excretion, drug combination, and severity of the particular condition and can be determined by one of skill in the art. The dosage can be adjusted by the individual physician in the event of any contraindications. Dosages can vary, and can be administered in one or more dose administrations daily, for one or several days. Guidance can be found in the literature for appropriate dosages for given classes of pharmaceutical products.

The compositions are administered in a number of ways depending on whether local or systemic treatment is desired, and on the area to be treated. The compositions are administered via any of several routes of administration, including topically, orally, parenterally, intravenously, intraperitoneally, intramuscularly, subcutaneously, intracavity, transdermally, intra-bronchially, nebulization/inhalation, or by installation via bronchoscopy. Optionally, the composition is administered by oral inhalation, nasal inhalation, or intranasal mucosal administration. Administration of the compositions by inhalant can be through the nose or mouth via delivery by spraying or droplet mechanism. For example, in the form of an aerosol inhalant, a nasal spray or a nebulizer solution. Effective doses for any of the administration methods described herein can be extrapolated from dose-response curves derived from in vitro or animal model test systems.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including in the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLE I

MCC is a critical defense mechanism of the airways to maintain surface hygiene. Deterioration of MCC is a key contributor to the pathogenesis of respiratory diseases. CF is an inherited autosomal recessive disorder presenting with obstructive lung disease characterized by chronic airway inflammation, frequent infectious exacerbations and bronchitis. CF is caused by mutations in CFTR, an epithelial anion channel that conducts chloride and bicarbonate ions to support surface water transport needed for airway hydration and mucociliary clearance (MCC). CF airways are poorly hydrated with highly viscous mucus and delayed mucociliary clearance that favors colonization by pathogenic bacteria and chronic inflammation.

Methods

Chamber Electrophysiology to Determine CFTR Function in Primary Human Airway Epithelial Cells and Tissues Human sample use was approved by the Institutional Review Board at the University of Alabama Birmingham. Primary human bronchial epithelial (HBE) cells were derived from lung explants after written informed consent from CF and non-CF subjects by methods described in Van Goor et al. ("Rescue of CF airway epithelial cell function in vitro by a CFTR potentiator VX-770" *Proc Natl Acad Sci USA*, 106:18825-18830 (2009)); and Rowe et al. ("DeltaF508 CFTR processing correction and activity in polarized airway and non-airway cell monolayers," *Pulm Pharmacol Ther* 23:268-278 (2010)). Primary human airway cells were grown at an air-liquid interface until terminally differentiated. Short-circuit current (Isc) was measured under voltage clamp conditions using MC8 clamps and P2300 Using chambers (Physiologic Instruments, San Diego, Calif.) (Rowe et al.). Stable plateaus of at least 10 min were achieved before addition of each reagent. Isc measurements in human airway explants were conducted following dissection of mucosal layer, and performed as described in cells with the exception of use of P2307 tissue mounts.

Cigarette Smoke Exposure

Cells and ferret airways were subjected to 3R4F (University of Kentucky) CS exposure levels via an inExpose cigarette pump system (Scireq-USA, Tempe, Ariz.) at 3 L/minute using flexiWare6 software. Machined containers were used to expose monolayers to WCS for 10-30 minutes. Air control monolayers were placed in a clean air current chamber replica.

α-7 nAChR Western Blots

For Western blotting, cell lysates from 16-HBE cells or ferret lungs were normalized for protein content, electrophoresed under SDS-PAGE conditions, and α-7 nAChR detected by chemiluminescence using a commercially available antibody. Data were normalized to tubulin loading control and performed on three occasions for quantification.

Cigarette Smoke-Induced COPD in Ferrets

Age and gender-matched wild-type ferrets [*Mustela putorius* furo, females (0.6-0.8), males (1.2-2.0) kg in body weight] were procured from Marshall BioResources (North Rose, N.Y.) and randomly assigned to whole cigarette smoke exposure or air control groups. Following a brief period of acclimatization and training, ferrets were restrained in customized male and female nose-only exposure tubes and an 8- or 36-port plenum connected to mainstream smoke output. Ferrets were exposed to 60 min of smoke from 3R4F research cigarettes, twice daily for six months. Cigarette smoke was generated by an automated cigarette smoke generator (SCIREQ, InExpose model (Montreal, Calif.) with a 24-cigarette auto-loading carousel. Such cigarette smoke intensity causes COPD pathology in these animals that closely resembles human patients (Raju et al. "A ferret model of COPD-related chronic bronchitis," *JCI Insight* 1:e87536 (2016)).

In Vivo CFTR Measurement Using Nasal Potential Difference Method (NPD)

CFTR function was measured using NPD, a method that is routinely used for cystic fibrosis diagnosis in the clinic. Under anesthesia, a small amount of lidocaine gel was placed on the exterior of the nare to inhibit sneeze response. The left nare was cannulated with PE-90 tubing pulled to a tip diameter of 0.30 mm. The potential difference anode was connected via an agar-filled 18G needle to a calomel/KCl cell connected to a high impedance voltmeter (VF-1; World Precision Instruments (Sarasota, Fla.)). Ringer's solution (baseline measurement), Ringer's plus amiloride (100 µm), a Cl— free solution containing $K_2HPO_4$ (2.4 mM), $KH_2PO_4$ (0.4 mM), Na Gluconate (115 mM), $NaHCO_3$ (25 mM), and Ca2 Gluconate (1.24 mM) with amiloride, and a Cl—-free solution plus forskolin (20 µM) or, GTS-21 (100 µM) were sequentially perfused at a rate of 3.0 ml/hr for at least 6 min each or until a stable potential was achieved. A Powerlab analog to digital converter and LabChart 7.0 software (AD Instruments (Sydney, AU) was used for analysis, as previously described for human studies (Solomon et al. "An international randomized multicenter comparison of nasal potential difference techniques," *Chest*, 138:919-928 (2010)). CFTR-dependent chloride transport was measured as the change in potential difference following perfusion with chloride-free solution plus forskolin.

Ex Vivo Micro-Optical Coherence Tomography (µ-OCT) Imaging

The µOCT system was used to study mucociliary clearance parameters in ferret airway explants. µOCT supports simultaneous acquisition of data regarding airway surface liquid height, ciliary beat frequency and mucociliary transport (Raju et al. "The Cystic Fibrosis Transmembrane Conductance Regulator Potentiator Ivacaftor Augments Mucociliary Clearance Abrogating Cystic Fibrosis Transmembrane Conductance Regulator Inhibition by Cigarette Smoke," *Am J Respir Cell Mol Biol*, 56:99-108 (2017)). In the current study, cross-sectional images of 0.5 mm×0.5 mm (x, z) were acquired at a spatial resolution of 2 µm×2 µm×1 µm (x,y,z) and a speed of 32-128 frames/sec. The methods used to measure ASL depth and ciliary beat frequency (CBF) from the µOCT data are available (See, for example, Conger Jr. et al., *JAMA Otolaryngol. Head Neck Surg.* 139(8): 822-827 (2013)).

Statistics

For quantitative measures including in vitro studies and potential difference testing, descriptive statistics were computed and means compared using Student's t-test or ANOVA, as appropriate. Statistical tests were two-sided and performed at a 5% significance level using GraphPad Prism (La Jolla, Calif.). Error bars designate SEM unless indicated otherwise.

Results

Figure 1B:
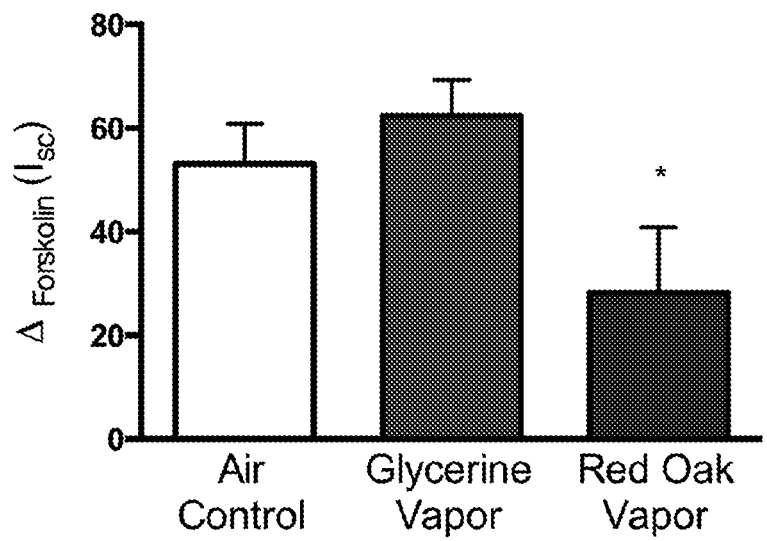
FIG. 1B shows the results of exposing HBE cells to vapor from commercial e-cigarette blend (Red Oak) and matched vehicle (Glycerin). Forskolin-induced anion transport via CFTR channels that is needed for optimum MCC is shown.
Figure 1C:
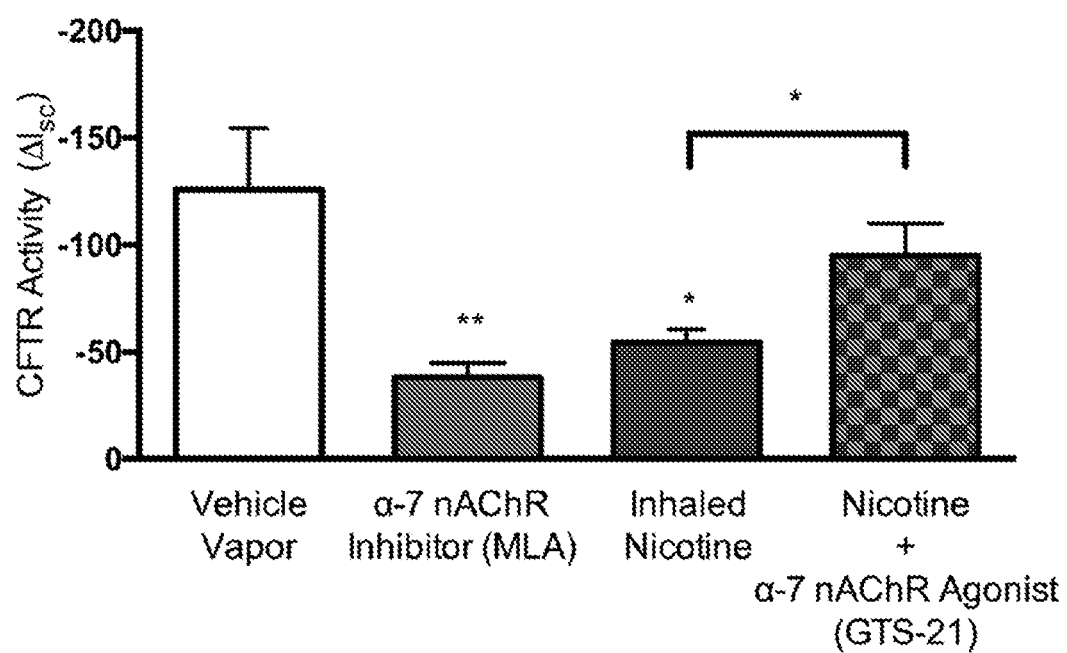
FIG. 1C shows the results of exposing matched ferret tracheal segments to vehicle, α-7 nAChR inhibitor MLA, and nicotine vapor with and without α-7 nAChR agonist GTS-21 for 1 hr, followed by estimation of CFTR activity in response to forskolin. N=6 per condition, * P<0.05, **P<0.01. GTS-21 restored CFTR-dependent Isc (short circuit current measurements) affected by nicotine vapor exposure confirming the in vitro findings shown in FIGS. 1 A-B.

FIG. 1A shows the effects of treating primary human bronchial epithelial (HBE) cells with vehicle (water vapor), α-7 nAChR inhibitor MLA, and nicotine vapor with and without α-7 nAChR. Forskolin-induced anion transport via CFTR channels that is needed for optimum MCC is shown. These data suggest that loss of α-7 nAChR signaling impacts CFTR function and as such α-7 nAChR activation restores CFTR function. FIG. 1B shows the results of exposing HBE cells to vapor from commercial e-cigarette blend (Red Oak) and matched vehicle (Glycerin). FIG. 1C shows the results of exposing matched ferret tracheal segments to vehicle, α-7 nAChR inhibitor MLA, and nicotine vapor with and without α-7 nAChR agonist GTS-21 for 1 hr, followed by estimation of CFTR activity in response to forskolin. N=6 per condition, * $P<0.05$, ** $P<0.01$. GTS-21 restored CFTR-dependent Isc (short circuit current measurements)

Figure 2A:
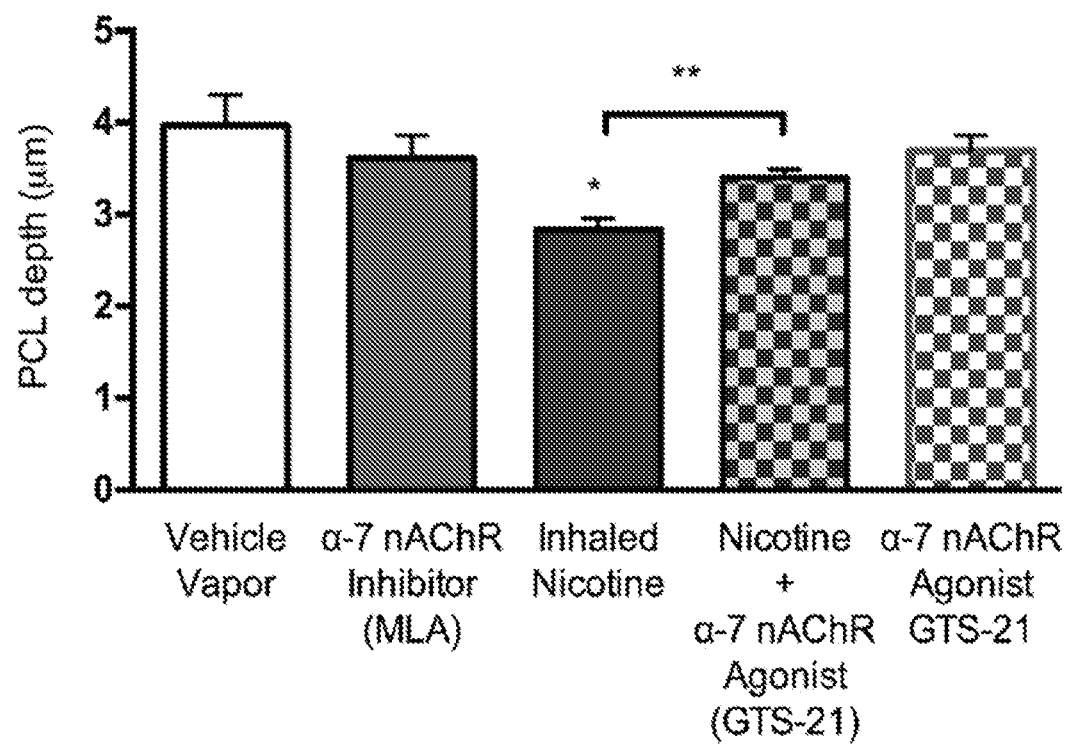
FIGS. 2A-B show that GTS-21 augments mucosal surface hydration in nicotine-exposed ferret trachea, as revealed by one micron resolution optical coherence tomography (μOCT) imaging. Matched ferret tracheal segments were exposed to vehicle (water vapor), α7nAChR inhibitor MLA, and nicotine vapor with and without α7nAChR agonist GTS-21 for 1 hr. Surface hydration is expressed as periciliary liquid layer (PCL) depth, and mucociliary transport rate (MCT, FIG. 2B). Data were derived from at least 5 measures per segment, and 4 segments per condition. *P<0.05, **P≤0.01. These data provide direct evidence that promotion of α-7 nAChR signaling with pharmacologic agents directly benefits mucosal surface hydration (PCL depth) significantly enhancing MCC.
Figure 2B:
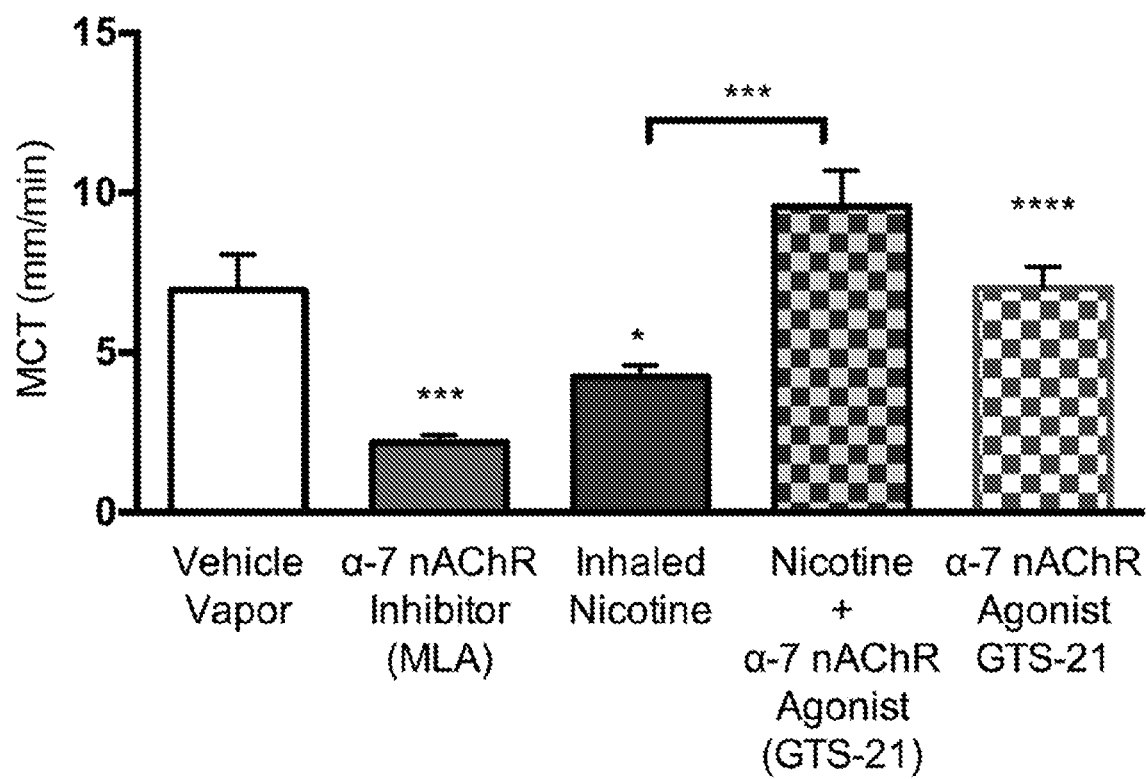

As shown in FIGS. 2A-B, GTS-21 augments mucosal surface hydration in nicotine-exposed ferret trachea, as revealed by one micron resolution optical coherence tomography (µOCT) imaging. Matched ferret tracheal segments were exposed to vehicle (water vapor), α7nAChR inhibitor MLA, and nicotine vapor with and without α7nAChR agonist GTS-21 for 1 hr. Surface hydration was expressed as periciliary liquid layer (PCL) depth, and mucociliary transport rate (MCT, FIG. 2B). Data were derived from at least 5 measures per segment, and 4 segments per condition. * $P<0.05$, ** $P<0.01$. These data provide direct evidence that promotion of α-7 nAChR signaling with pharmacologic agents directly benefits mucosal surface hydration (PCL depth) while significantly enhancing MCC, thus promoting mucus transport, which is critical for defending against pathogens and preventing airways from getting obstructed by excessive mucus.

Figure 3A:
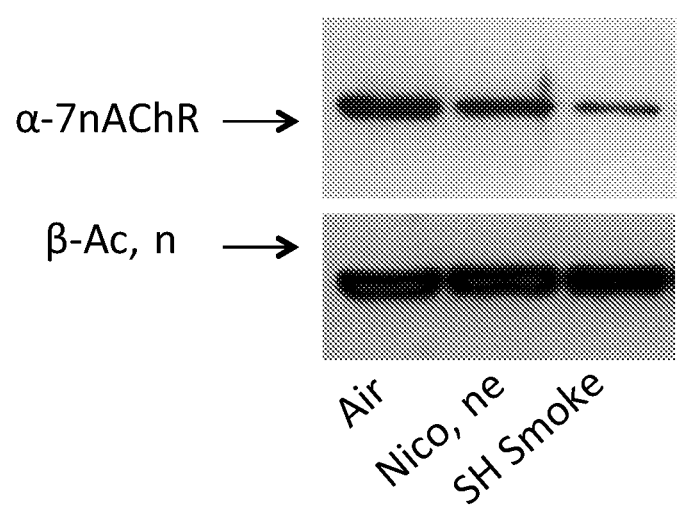
FIGS. 3A-B show that exposure of human airway epithelial cells to cigarette smoke decreases α-7 nAChR expression in human airway epithelial cells and this is associated with decreased CFTR ion transport as expected based on data shown in FIG. 1A & FIG. 1C.
Figure 3B:
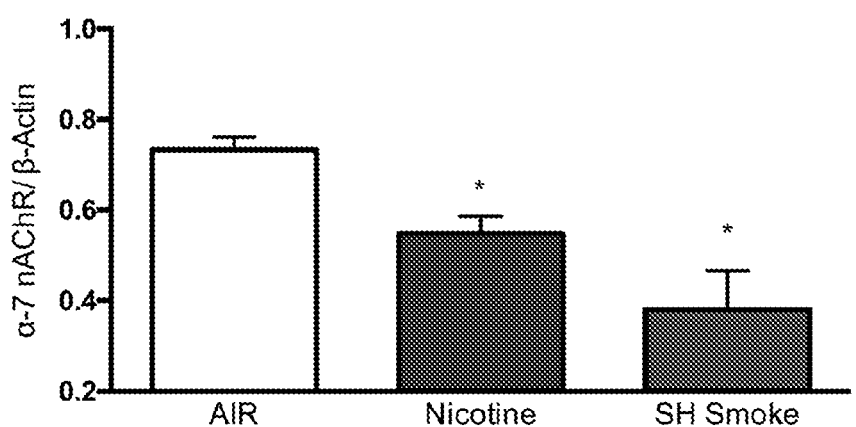

Smokers and COPD patients exhibit decreased CFTR function. This is especially true in patients with a chronic bronchitis phenotype that is very similar to that of cystic fibrosis (Raju et al. "Acquired Cystic Fibrosis Transmembrane Conductance Regulator Dysfunction in Chronic Bronchitis and Other Diseases of Mucus Clearance," *Clin. Chest Med.* 37: 147-158 (2016)). Therefore, experiments were performed to determine whether α-7 nAChR agonists stimulate CFTR ion transport and could serve to reduce COPD symptoms. It was established that α-7 nAChRs are critical for CFTR ion transport by blocking these receptors with MLA, a specific α-7 nAChR inhbitor, and quantifying CFTR function using an Ussing chamber electrophysiogical assay, as described above. Similarly, when α-7 nAChR was desensitized by nicotine or, secondhand smoke (SH Smoke) administration, decreased CFTR function was observed. As shown in FIGS. 3A-B, exposure of human airway epithelial cells to cigarette smoke decreases α-7 nAChR expression in human airway epithelial cells and this is associated with decreased CFTR ion transport as expected, based on data shown in FIG. 1A & FIG. 1C.

Figure 4:
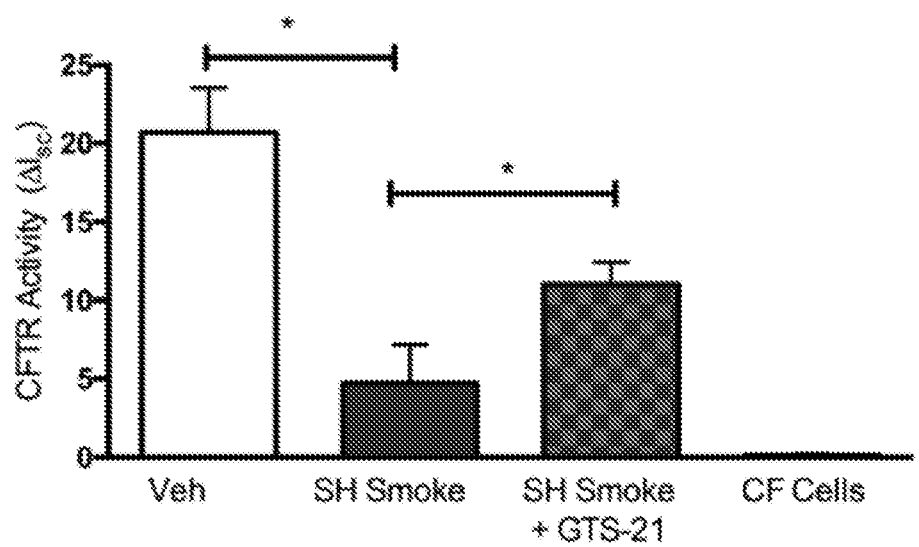
FIG. 4 shows that administration of GTS-21 to human airway epithelial cells was protective against smoke-induced CFTR defects beneficiating chronic smokers and COPD patients.

As shown in FIG. 4, administration of GTS-21 to human airway epithelial cells was protective against smoke-induced CFTR defects beneficiating chronic smokers and COPD patients.

Figure 5A:
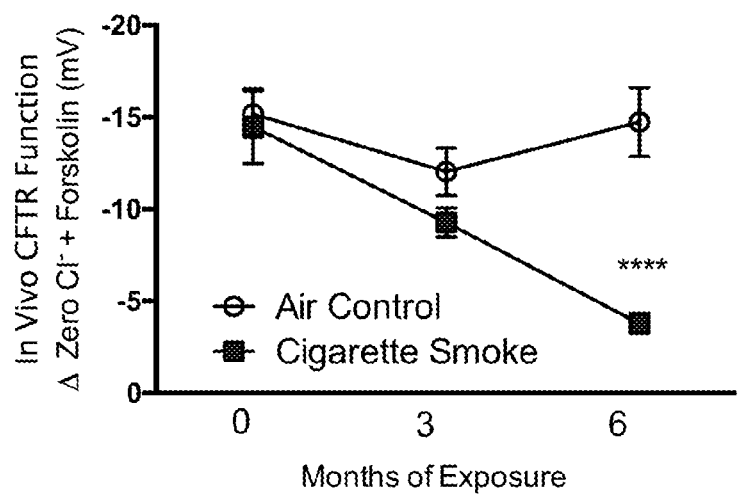
FIG. 5A shows that a ferret model of chronic obstructive pulmonary disease (COPD) exposed to chronic cigarette smoke for 6 months exhibited CFTR dysfunction similar to that observed in COPD patients.
Figure 5B:
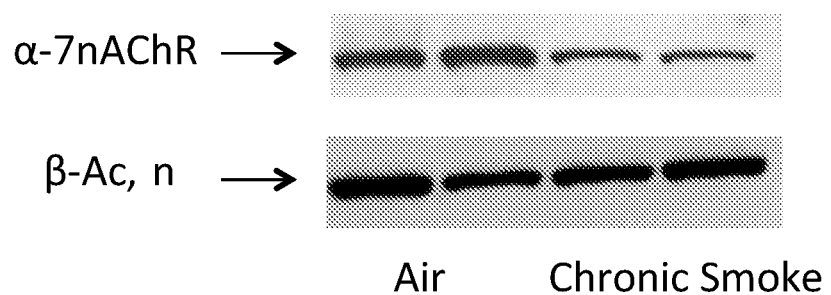
FIG. 5B shows that diminished CFTR function in a ferret model of COPD correlated with decreased α-7 nAChR.
Figure 5C:
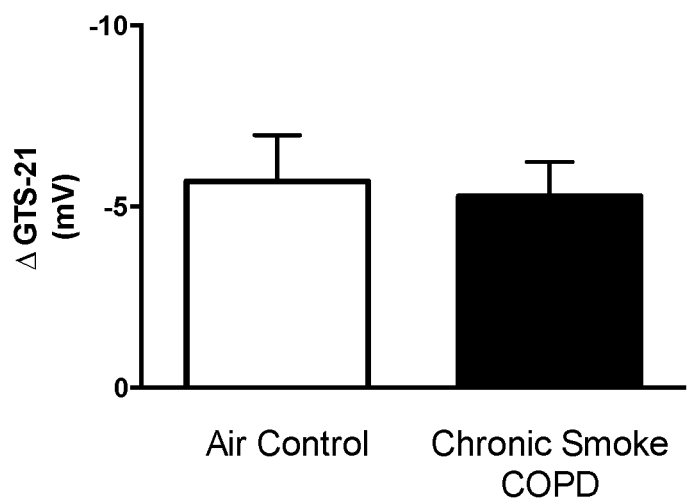
FIG. 5C shows that in vivo administration of GTS-21 to a ferret COPD model restored CFTR function despite active smoking status and reduced α-7 nAChR expression. In vivo CFTR activity was measured by by nasal potential difference (NPD), a method routinely used for in vivo quantification of CFTR function and diagnosis of CF disease.

As shown in FIG. 5A, a ferret model of chronic obstructive pulmonary disease (COPD) (Raju et al. "A ferret model of COPD-related chronic bronchitis," JCI Insight 1:e87536 (2016)) exposed to chronic cigarette smoke for 6 months exhibited CFTR dysfunction similar to that observed in COPD patients. FIG. 5B shows that diminished CFTR function in a ferret model of COPD correlated with decreased α-7 nAChR. FIG. 5C shows that in vivo administration of GTS-21 to a ferret COPD model restored CFTR function despite active smoking status and reduced α-7 nAChR expression. In vivo CFTR activity was measured by nasal potential difference (NPD), as described above.

Figure 6A:
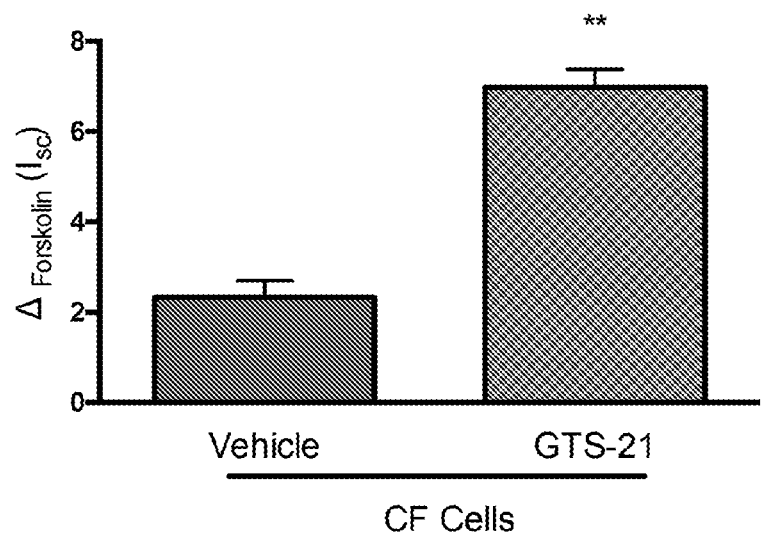
FIG. 6A shows that when bronchial epithelial cells from cystic fibrosis (CF) patients with F508del mutations (CF48) were treated with GTS-21 (30 min. pre-treat exposure) there was an increase in CFTR ion transport in response to forskolin, a CTFR activator. These data provide evidence that, while an α-7 nAChR agonist may not correct the genetic defect in CF patients, it increases the sensitivity of CFTR channels (despite structural defects) to further activation by cellular cAMP.
Figure 6B:
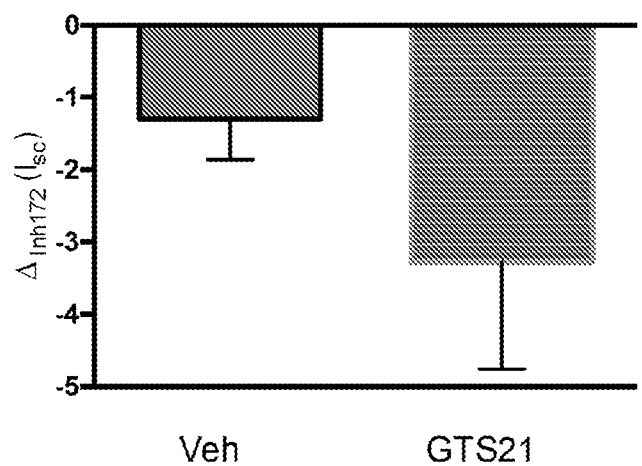
FIG. 6B shows that CFTR activation was quantified in response to a specific blocker, CFTR Inhibitor 172, that directly binds to CFTR, thereby accounting for the magnitude of benefit that is directly related to CFTR activity.

As shown in FIG. 6A, when bronchial epithelial cells from cystic fibrosis (CF) patients with F508del mutations (CF48) were treated with GTS-21 (30 min. pre-treat exposure) there was an increase in CFTR ion transport in response to forskolin, a CTFR activator. These data provide evidence that, while an α-7 nAChR agonist may not correct the genetic defect in CF patients, the agonist increases the sensitivity of CFTR channels (despite structural defects) to further activation by cellular cAMP. FIG. 6B shows that CFTR activation was quantified in response to a specific blocker, CFTR Inhibitor 172, that directly binds to CFTR, thereby accounting for the magnitude of benefit that is directly related to CFTR activity.

Figure 7:
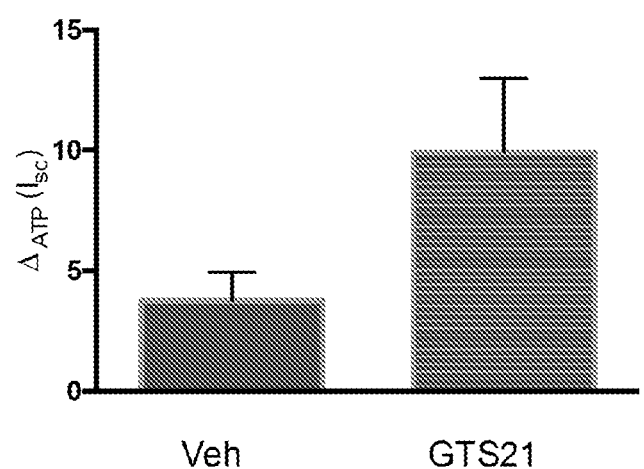
FIG. 7 shows that, upon addition of GTS-21, there was an increase in ATP responsive ion transport in CF cells. In airway epithelial cells ATP activates calcium-dependent chloride (CaCC) channels. These data indicate that membrane stabilization by GTS-21 can benefit transport through chloride channels other than CFTR, suggesting that improvements observed in airway hydration and MCC could also be due to chloride ion channels other than CFTR.

As shown in FIG. 7, upon addition of GTS-21, there was an increase in ATP responsive ion transport in CF cells. In airway epithelial cells, ATP activates calcium-dependent chloride (CaCC) channels. These data indicate that membrane stabilization by GTS-21 can benefit transport through chloride channels other than CFTR, suggesting that improvements observed in airway hydration and MCC could also be due to chloride ion channels other than CFTR.

Figure 8:
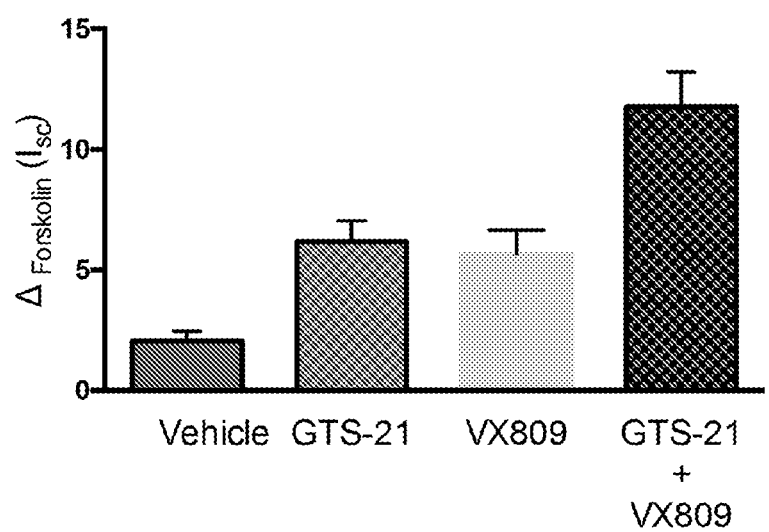
FIG. 8 shows the synergistic function of GTS-21 with a CFTR corrector that corrects underlying genetic defects by increasing the surface localization of mutated CFTR proteins. While GTS-21 alone can augment CFTR ion transport following forskolin treatment, its benefits are vastly increased when used in CF cells that were treated with VX809, a CFTR corrector drug. These data also suggest that GTS-21 could be useful in patients who are already using CFTR therapeutics.

FIG. 8 shows the synergistic function of GTS-21 with a CFTR corrector that corrects underlying genetic defects by increasing the surface localization of mutated CFTR proteins. While GTS-21 alone can augment CFTR ion transport following forskolin treatment, its benefits are vastly increased when used in CF cells that were treated with VX809, a CFTR corrector drug. These data suggest that GTS-21 could be useful in patients who are already using CFTR therapeutics. Therefore, α-7 nAChR agonists could serve as stand-alone CF therapy or, could be used in combination with existing CF therapeutics to address airway symptoms.

Figure 9A:
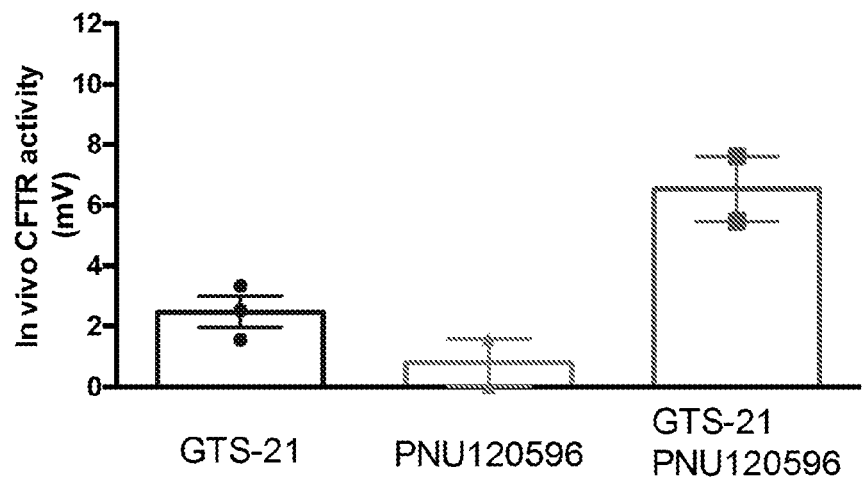
FIG. 9A shows that activation of α-7 nAChRs enhanced CFTR function in rat airways as determined by NPD. These data confirm that in a live animal, activation of α-7 nAChRs can be used to augment CFTR function. Interestingly, activation of α-7 nAChRs with positive allosteric modulator compound (PNU120596) was similar to that of full agonist (GTS-21).
Figure 9B:
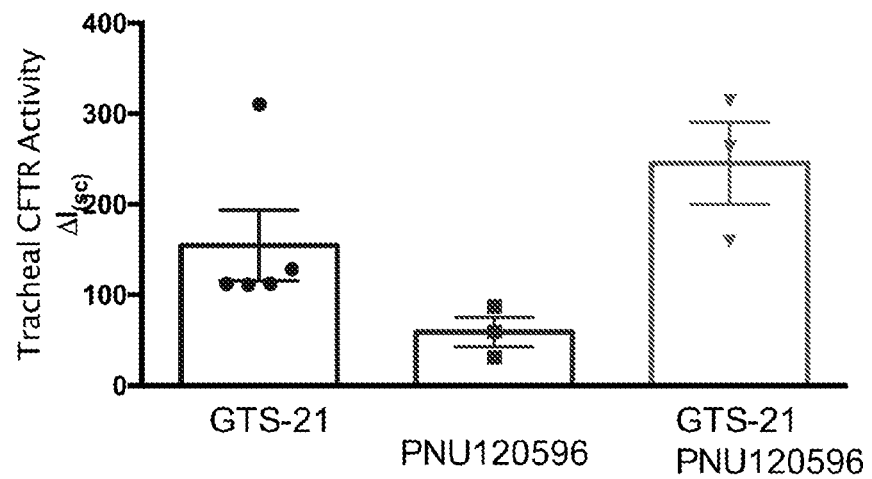
FIG. 9B shows that activation of α-7 nAChRs enhanced CFTR function in rat airways as measured Ussing chamber electrophysiology using isolated tracheal explants.

FIG. 9A shows that activation of α-7 nAChRs enhanced CFTR function in rat airways as determined by NPD. These data confirm that in a live animal, activation of α-7 nAChRs can be used to augment CFTR function. Interestingly, activation of α-7 nAChRs with positive allosteric modulator compound (PNU120596) was similar to that of full agonist (GTS-21). FIG. 9B shows that activation of α-7 nAChRs enhanced CFTR function in rat airways as measured Ussing chamber electrophysiology using isolated tracheal explants.

As shown herein, cigarette smoke exposure decreases CFTR activity, thus mimicking COPD patients (Raju et al. "Cigarette smoke induces systemic defects in cystic fibrosis transmembrane conductance regulator function," *Am J Respir Crit Care Med*, 188:1321-1330 (2013)). See, for example, FIGS. 3A, 3B and 4, where exposure to cigarette smoke or, nicotine reduced CFTR function in vitro. This was further confirmed in an in vivo model of COPD in ferrets (Raju et al. "A ferret model of COPD-related chronic bronchitis," *JCI Insight* 1:e87536 (2016)) where CFTR function was found to be defective (FIG. 5A). In both human airway epithelial cells as well as ferret lungs, altered CFTR function correlates with decreased α-7 nAChR in the lungs (FIGS. 3 A, 3B and 5B). Hence, when GTS-21 was administered to human cells (FIG. 4), ferret airways (in vitro) and ferret airways in vivo (FIG. 5C) there was substantial restoration of smoke induced defects on CFTR ion transport.

As observed in FIGS. 2A and 2B respectively, pharmacologic augmentation of α-7 nAChR results in increased airway surface hydration as measured by periciliary liquid layer depth (PCL, FIG. 2A) that further promotes mucus transport (FIG. 2B), that is critical for defending against pathogens and preventing airways from getting obstructed by excessive mucus. As shown herein, analysis of human airway epithelial cells and ferret tracheal explants indicated that treatment with α-7 nAChR agonists, for example, GTS-21, results in significantly increased CFTR ion transport and rate of MCC. These data establish that agents that activate α-7 nAChR receptors in airways can be used to treat respiratory disorders and increase MCC in patients suffering from cystic fibrosis, COPD, asthma and other respiratory diseases.

What is claimed is:

1. A method of increasing mucus mucociliary clearance (MCC) in the airways of the lungs of a subject having decreased MCC comprising administering to the subject an effective amount of α-7 nicotinic acetylcholine receptor (nAChR) agonist wherein the α-7 nAChR agonist is an anabaseine (3,4,5,6-Tetrahydro-2,3'-bipyridine) derivative or wherein the α-7 nAChR agonist is a compound of Formula I

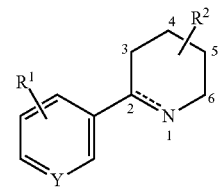

or a pharmaceutically acceptable salt thereof, wherein the dotted line between the 1-and 2-positions of the 6-membered cyclic ring containing nitrogen atom represents an optional bond; Y is nitrogen or carbon; $R^1$ is hydrogen or $C_1$-$C_4$ alkyl; and $R^2$ is hydrogen, $C_1$-$C_4$ alkyl, or =CH—X, wherein X is napthyl optionally substituted by N,N-dialkylamino having 1 to 4 carbons in each of the alkyls, styryl optionally substituted by N,N-dialkylamino having 1 to 4 carbons in each of the aklyls, furyl, furylacrylyl or

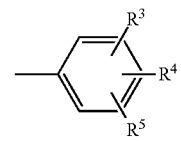

wherein $R^3$, $R^4$, and $R^5$ are each selected from hydrogen, $C_3$-$C_4$ alkyl, $C_1$-$C_6$ alkoxy optionally substituted by N,N dialkylamino having 1 to 4 carbons in each of the alkyls, amino, cyano, N,N-dialkylamino having 1 to 4 carbons in each of the alkyls, halo, hydroxyl and nitro.

2. The method of claim 1, wherein the subject has a respiratory disorder or is at risk of developing a respiratory disorder.

3. The method of claim 1, wherein the α-7 nAChR agonist is a compound of Formula III

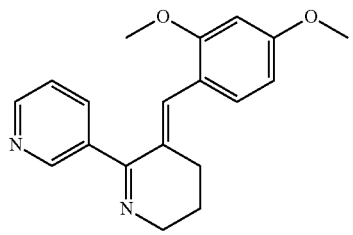

III or a pharmaceutically acceptable salt thereof.

4. The method of claim 2, wherein the respiratory disorder is selected from the group consisting of cystic fibrosis, chronic obstructive pulmonary disease (COPD), asthma, bronchitis, and a respiratory infection.

5. The method of claim 1, wherein the α-7 nAChR agonist increases ion transport in the subject.

6. The method of claim 5, wherein ion transport is increased through calcium-activated chloride channels in the subject.

7. The method of claim 6, wherein CFTR ion transport is increased in the subject.

8. The method of claim 1, further comprising administering a second therapeutic agent to the subject.

9. The method of claim 8, wherein the second therapeutic agent is a CFTR modulator.

10. The method of claim 1, wherein a pharmaceutically acceptable composition comprising the α-7 nAChR agonist is administered to the subject.

11. The method of claim 1, wherein the α-7 nAChR agonist is administered orally, parenterally, intravenously, intraperitoneally or by inhalation.

12. The method of claim 11, wherein the α-7 nAChR agonist is administered using an inhaler selected from the group consisting of a nebulizer, a metered-dose inhaler and a dry powder inhaler.

13. The method of claim 10, wherein the composition comprises liposomes comprising the α-7 nAChR agonist.

14. The method of claim 1, wherein the α-7 nAChR agonist is administered to the subject daily.

15. The method of claim 1, wherein multiple doses of the α-7 nAChR agonist are administered to the subject.

* * * * *

UNITED STATES PATENT AND TRADEMARK OFFICE
CERTIFICATE OF CORRECTION

PATENT NO. : 11,096,932 B2
APPLICATION NO. : 16/338150
DATED : August 24, 2021
INVENTOR(S) : Sammeta Vamsee Raju, Lawrence Rasmussen and Steven Mark Rowe It is certified that error appears in the above-identified patent and that said Letters Patent is hereby corrected as shown below:

In the Specification

Column 1, After Line 6, Insert:
--STATEMENT REGARDING SPONSORED RESEARCH
Research for this invention was supported by awards from the Cystic Fibrosis Foundation.--

Signed and Sealed this
Twelfth Day of November, 2024

Katherine Kelly Vidal
*Director of the United States Patent and Trademark Office*